United States Patent [19]

Teng et al.

[11] Patent Number: 5,275,933

[45] Date of Patent: Jan. 4, 1994

[54] TRIPLE GRADIENT PROCESS FOR RECOVERING NUCLEATED FETAL CELLS FROM MATERNAL BLOOD

[75] Inventors: Nelson N. H. Teng, Hillsborough; Neelima M. Bhat, Cupertino; Marcia M. Bieber, Los Altos Hills, all of Calif.

[73] Assignee: The Board of Trustees of the Leland Stanford Junior University, Stanford, Calif.

[21] Appl. No.: 951,628

[22] Filed: Sep. 25, 1992

[51] Int. Cl.$^5$ ................................. A01N 1/02
[52] U.S. Cl. ............................. 435/2; 210/789
[58] Field of Search ....................... 435/2; 210/789

[56] References Cited

U.S. PATENT DOCUMENTS

| | | | |
|---|---|---|---|
| 3,852,194 | 12/1974 | Zine, Jr. | 210/83 |
| 4,147,628 | 4/1979 | Bennett et al. | 210/83 |
| 4,153,739 | 5/1979 | Kessler | 427/2 |
| 4,190,535 | 2/1980 | Luderer et al. | 210/83 |
| 4,255,256 | 3/1981 | Ferrante et al. | 210/730 |
| 4,350,593 | 9/1982 | Kessler | 210/516 |
| 4,675,286 | 6/1987 | Calenoff | 435/7 |
| 4,751,001 | 6/1988 | Saunders | 210/516 |
| 4,822,745 | 4/1989 | Burns et al. | 436/63 |
| 4,927,750 | 5/1990 | Dorn | 435/2 |

FOREIGN PATENT DOCUMENTS

WO91/14768 10/1991 PCT Int'l Appl. .

OTHER PUBLICATIONS

Bianchi et al; Direct Hybridization to DNA from Small Numbers of Flow-Sorted Nucleated Newborn Cells, Cytometry 8: pp. 197-202 (1987).

Iverson et al; Detection and Isolation of Fetal Cells From Maternal Blood Using the Flourescence-Activated Cell Sorter (FACS), Prenatal Diagnosis, vol. 1, pp. 61-73 (1981).

Herzenberg et al; Fetal Cells in the Blood of Pregnant Women: Detection and Enrichment by Fluorescence-Activated Cell Sorting Proc. Natl. Acad. Sci USA, vol. 76, No. 3 pp. 1453-1455, Mar. 1979.

Bianchi et al; Isolation of Fetal DNA from Nucleated Erythrocytes in Maternal Blood Proc. Natl. Acad. Sci. USA, vol. 87, pp. 3279-3283, May 1990 Medical Sciences.

Corash et al; Separation of Erythrocytes According to Age on a Simplified Density Gradient J. Lab. Clin. Med, Jul. 1974, vol. 84 No. 1, pp. 147-151.

*Primary Examiner*—Douglas W. Robinson
*Assistant Examiner*—Sandra Saucier
*Attorney, Agent, or Firm*—Bertram I. Rowland

[57] ABSTRACT

Nucleated fetal cells such as nucleated fetal red blood cells are separated from maternal blood with a discontinuous triple gradient gel and centrifugation. Nucleated fetal red blood cells are collected at an interface between a gel layer having a density in the range of from 1.105 to 1.110 g/mL and the second layer having a density in the range of from 1.075 to 1.085 g/mL, and maternal granulocytes are collected at an interface between a gel layer having a density in the range of from 1.115 to 1.125 g/mL and a layer having a density in the range of from 1.105 to 1.110 g/mL. This allows separation of fetal cells for testing from the maternal blood rather than the placenta or amniotic fluid, reducing the risk of sample collection and facilitating routine testing of fetal cells for evidence of genetic defects.

4 Claims, No Drawings

TRIPLE GRADIENT PROCESS FOR RECOVERING NUCLEATED FETAL CELLS FROM MATERNAL BLOOD

FIELD OF THE INVENTION

This invention relates to a method or process for separating nucleated fetal red blood cells and other nucleated fetal cells from maternal blood using a discontinuous or step triple gradient gel.

BACKGROUND OF THE INVENTION

The examination of fetal cells for early detection of fetal diseases and genetic abnormalities is undertaken in approximately one out of every thirty pregnant women. The main indication is maternal age (over 35 years). The tests may involve DNA gene typing or, more commonly, the use of live fetal cells for chromosomal karyotyping.

Fetal cells are usually obtained by amniocentesis, the removal of amniotic fluid from the amniotic cavity within the amniotic sac or placenta. The procedure presents a risk of harm to the fetus, particularly after the first trimester of pregnancy. The risk to the fetus together with the high cost of the procedure have prevented the establishment of examination of fetal cells for early detection of abnormalities as a routine procedure in pregnancy.

In the late 1970s and early 1980s, Herzenberg and his colleagues reported that fetal cells were present in maternal blood as early as 15 weeks gestation. The authors separated maternal and fetal cells using fluorescence-activated cell sorting (FACS) by staining maternal blood for a distinguishing paternal HLA antigen. The authors state that the demonstration that fetal cells enter maternal circulation and can be isolated by FACS-enrichment procedures could have practical significance in enabling karyotyping without the need for amniocentesis. The authors state that this would be possible if the frequency of successful isolation of cells at 15 weeks is sufficiently high and the cells could be induced to divide (enter metaphase). Furthermore, extensive HLA typing reagents, or other cell surface reagents would need to be developed to distinguish maternal and fetal cells. To date, the technique has not been successfully adapted for use as a clinical technique for either karyotyping or fetal DNA analysis.

Recently, fetal cells present in maternal blood have been used to perform analysis of genes present in the fetus. In one technique, the maternal and fetal cells were not separated and the DNA from the cell mixture is amplified with Y chromosome-specific primers to determine whether the fetus is male. It has been suggested that DNA amplification techniques can also be performed to detect gene sequences associated with disease in this manner. Of course, the method cannot be used where the mother is a carrier for the trait.

Prior to this invention, amniotic fluid has been the only source of antenatal cells to provide a sufficient number of live cells for karyotyping. Furthermore, DNA analysis methods have only been possible in relatively limited situations which depend on particular differences in maternal and fetal cells, e.g. presence of the Y chromosome in the fetus or presence of HLA-A2 antigen on fetal, but not maternal, cells.

DESCRIPTION OF THE PRIOR ART

Herzenberg and his colleagues have described methods for separating maternal and fetal cells in maternal blood using fluorescence-activated cell sorting (FACS). In Herzenberg et al, *Proc.Natl.Acad.Sci.USA* 76:1453-1455 (1979), cells in blood samples from 15-week pregnant HLA A2-negative women were stained for HLA A2 antigen. Stained cells were separated by FACS and collected to enrich the population of fetal cells. Although the technique was demonstrated to effectively identify male, HLA A2-positive cells in maternal blood, to date the technique has not been successfully adapted for general applicability. In Iverson et al, *Prenat.Diag.* 1:61-73 (1981), peripheral blood lymphocytes (PBLS) from either 15 week or 21 to 25 week pregnant women were examined. If the woman was HLA A2-negative, her cells were stained with anti-HLA A2 reagents, sorted by FACS onto microscope slides (for fetuses who were HLA A2-positive), stained with quinacrine and examined microscopically for Y chromatin-positive cells. The authors report that fetal cells enter the maternal circulation as early as 15 weeks gestation.

Simons, PCT patent application WO 91/14768 describes a method made after our invention for separating fetal cells from maternal cells based on the non-reactivity of the fetal cells to an antibody specific for a cell surface antigen encoded by a non-transmitted allele. Fetal cells are separated from cell concentrates obtained using density gradient methods. Fetal cell separations disclosed include solid phase bead and plate separations and FACS separations.

Bianchi et al, *Cytometry* 8:197-202 (1987) report a technique that allows direct hybridization to the DNA of cells which were flow sorted onto nitrocellulose filters which eliminates the need for a DNA isolation step. The method was performed on human cord blood. The authors state that the technique is useful in situations where there is a limited amount of DNA available for analysis such as for fetal cells recovered from maternal blood.

U.S. Pat. No. 4,675,286 (to Calenoff, issued Jun. 23, 1987) describes a method for obtaining fetal cells for diagnostic examination in which detached cells from the uterine cavity and outer surface of the amniotic sac are incubated with a separation antibody which binds preferentially to either fetal or maternal cells. The antibody can be bound to an insoluble support or conjugated with a fluorescent label and removed with a cell sorter to effect separation.

Density gels and centrifugation are routinely used to separate certain populations or subpopulations of blood cells from adult blood. A variety of these methods including use of a one step density gradient are summarized in U.S. Pat. No. 4,255,256 (to Ferrante et al, issued Mar. 10, 1981), for example. In these methods, the cell mixture is placed on the surface of a gel in a tube, and the components are settled into layers by gravity or centrifugation. Single density gradient gels generally yield two zones, one at the surface of the gel and the other at the bottom. Continuous density gradient gels yield zones of cells throughout the gel separated by density. The patent also describes discontinuous density gradients with two or more separating solutions of different densities layered on top of one another. The densities are selected to provide a discontinuous gradient over a desired range. In the procedures, nucleated cells such as lymphocytes are usually collected as a mixture separated from mature red blood cells.

Each of the above-described references and the publications cited therein are hereby incorporated by reference in their entireties into this application.

SUMMARY AND OBJECTS OF THE INVENTION

The method of this invention for separating nucleated fetal red blood cells from maternal blood mononuclear cells, granulocytes and mature red blood cells comprises applying maternal blood to a discontinuous gradient gel having at least first, second, and third layers. The first and second layers and the second and third layers form a first and a second interface therebetween, respectively. The first layer has a density in the range of from about 1.115 to about 1.125 g/mL. The second layer has a density in the range of from about 1.105 to about 1.110 g/mL. The third layer has a density in the range of from about 1.075 to about 1.085. The gel is subjected to separation forces such as gravity or centrifugation for a time sufficient to cause movement of nucleated fetal red blood cells to the first, upper interface and maternal granulocytes and nucleated fetal cells to the second, lower interface. The nucleated fetal cells can then be removed from the respective interface.

It is an object of this invention to provide a source of fetal cells for chromosome and DNA analysis for genetic defects and diseases which does not expose the mother or the fetus to the medical risks of sample collection from the placenta or amniotic fluid.

It is another object of this invention to provide a method for separating nucleated fetal cells from maternal blood which can be carried out as a simple routine by laboratory technicians.

DETAILED DESCRIPTION OF THE INVENTION

The terms 'first layer', 'second layer', and 'third layer' as used herein, are defined to identify the order of layers in the direction of the separating force, from most force to least force, the first layer being below the second layer in the force field. In a gravity separation process, the first layer is positioned below the second layer which is, in turn, below the third layer. In a centrifugal separation process, the second layer is positioned between the axis of spin and the first layer, and the third layer is positioned between the axis of spin and the second layer.

The method of this invention provides a method for isolating fetal cells from maternal blood, a method which does not expose the fetus to the risks of amniocentsis and villus biopsy sampling methods. It includes the steps of applying maternal blood to a discontinuous gel having the critical densities required to separate the target nucleated fetal red blood cells from maternal granulocytes, maternal blood mononuclear cells, mature red blood and other components in maternal blood and using a separation force such as gravity or centrifugal force to effect the separation. The separated cells can be removed from the gel for further processing and analysis.

The discontinuous gel can be prepared by standard procedures from conventional gradient gel compositions, and neither the method of preparing the gel nor the gradient gel composition, per se, is a part of this invention. Suitable gel compositions and methods for preparing the gels are described in U.S. Pat. Nos. 4,255,256 (issued Mar. 10, 1981 to Ferrante et al), 4,751,001 (issued Jun. 14, 1988 to Saunders), and 4,927,750 (issued May 22, 1990 to Dorn), for example, and the entire contents of these patents are hereby incorporated by reference. FICOLL compositions (Pharmacia Fine Chemicals, Sweden) are one type of suitable gel. These are neutral highly branched, high molecular weight polymers of sucrose. These polymers are generally mixed with a compound which forms a high density, low viscosity aqueous solution such as the iodinated low molecular weight compounds such as sodium metrizoate or sodium diatrizoate. Alternatively, the cell separation can be effected with solutions of sucrose, dextran, bovine serum albumin, or heavy salts such as cesium chloride. Suitable density gradient gels formed from colloidal silica having a non-toxic organic coating are described in U.S. Pat. No. 4,927,750.

Other compositions which can be included are barrier phases which can be used to establish a barrier between lighter and heavier layers such as described in U.S. Pat. Nos. 4,190,535, 3,852,194, 4,147,628, 4,350,593 and 4,153,739, for example.

The multiple layer, discontinuous density gradient gel can be constructed by conventional layering techniques wherein each density layer is successively applied, from the most dense on the bottom of a container to the least dense layer on the top. Conveniently, the most dense layer is added to the tube first.

The maternal blood can be collected at any stage during the pregnancy when it would normally contain nucleated fetal red blood cells. The cells are usually present after week 15 of pregnancy.

The maternal blood pretreated with heparin or another anticoagulant is preferably applied to the assembled gel layers, most preferably being applied to the top surface of the gel layers. However, the maternal blood can be applied to the bottom or at an intermediate level, if desired, since the blood components migrate in the separation force field to an interface with adjoining gel densities above and below the density of the blood component. Alternatively, the gradient layers can be sequentially added to maternal blood.

Nucleated fetal red blood cells will efficiently collect at an interface between a more dense layer and a less dense layer. The more dense layer has a density greater than that of nucleated fetal red blood cells but less than the density of granulocytes.

A system for simultaneously separating nucleated fetal red blood cells and nucleated fetal cells and maternal granulocytes from other maternal blood components would require at least first, second and third layers. The first and second layers form a first interface therebetween wherein nucleated fetal cells and maternal granulocytes collect. Maternal granulocytes will efficiently collect at an interface between a more dense layer and a less dense layer. In addition, the layer contains nucleated cells which are clearly fetal in origin. The cells may be fetal granulocytes or fetal trophoblast cells. The more dense layer has a density greater than that of the granulocytes but less than the effective density of mature red blood cells. The less dense layer has a density less than granulocytes but greater than nucleated fetal red blood cells. The second and third layers form a second interface therebetween wherein nucleated fetal red blood cells collect. As stated previously, nucleated fetal red blood cells will efficiently collect at an interface between a layer having a density greater than that of nucleated fetal red blood cells but less than the density of granulocytes and a layer having a density less than that of nucleated fetal red blood cells but greater than that of mononuclear cells.

We have discovered that the first layer in such a combination should have a density in the range of from about 1.115 to about 1.125 g/mL. The second layer should have a density in the range of from about 1.105 to about 1.110 g/mL. When the density of the second layer was greater than 1.110 g/mL, noticeable contamination with granulocytes occurred. The third layer should have a density in the range of from about 1.075 to about 1.085. Most preferred is the use of a gel having densities of 1.119, 1.107 and 1.077 for the first, second and third layers, respectively.

The gel layers are then exposed to a separation force field such as gravity or centrifugal force for a time sufficient to allow movement of the blood components to their respective densities. In the two layer system, the nucleated fetal red blood cells collect in the interface area, the granulocytes and mature red blood cells settling to the lowest level, and the maternal mononuclear cells collect at the highest level. In the three layer system, the nucleated fetal red blood cells collect at the middle interface, and nucleated fetal cells and maternal granulocytes collect at the lower interface.

The method of this invention can be easily carried out with conventional centrifuge tubes and laboratory centrifuges. The gels are then layered directly into a centrifuge tube, and the collected cells are removed from an intermediate layer by pipette, for example.

The collected cells are then processed by conventional procedures suitable for the analysis techniques to be used. For example, they can be bound to solid supports such as magnetic beads, or preferably, optically flat plates using fetal cell preferentially binding antibodies adhered to the substrates.

This invention is illustrated by the following specific but non-limiting examples, wherein the temperatures are given in degrees Centigrade and the percents are given as weight percents unless otherwise specified. Examples which have been reduced to practice in a laboratory are described in the past tense, and examples which are being constructively reduced to practice herein are described in the present tense.

EXAMPLE 1

Nucleated Fetal Red Blood Cell Separation

Eight mL of a suspension of human fetal liver cells (containing about $1 \times 10^8$ cells from fetal liver which had been teased apart) in a medium (Hank's balanced salt solution (HBSS) with 1% fetal calf serum (FCS)) was carefully layered onto a 4 mL of HISTOPAQUE-1077 (1.077 g/mL) (Sigma Diagnostics, St. Louis, Mo.) in 15 mL sterile polystyrene tubes.

Eight mL of the same suspension was carefully layered onto a discontinuous, double gradient with HISTOPAQUE-1119 (1.119 g/mL) (Sigma Diagnostics) at the bottom and HISTOPAQUE-1077 (2 mL each) at the top in 15 mL sterile polystyrene tubes.

The tubes were centrifuged at $700 \times g$ for 30 minutes. The cells at the interfaces were recovered, washed twice with PBS (phosphate buffer solution) and resuspended in HBSS.

Examination of the samples showed that in the single layer gradient gel system, the mature red blood cells and granulocytes settled to the bottom, and the mononuclear cells and nucleated red blood cells collected at or near the top of the gel layer. In the two layer gradient gel system, the mononuclear cells collected on the top surface, the nucleated fetal red blood cells and granulocytes collected at the interface between the two gel layers, and the mature red blood cells collected at the bottom of the tube.

This example shows that the nucleated fetal red blood cells, together with granulocytes, can be separated from a cell mixture containing mononuclear cells and mature red blood cells by using a discontinuous gradient gel with appropriate densities.

EXAMPLE 2

Nucleated Fetal Red Blood Cell Separation

The procedure of Example 1 was repeated with the two layer gel system. A second gel was prepared having a discontinuous, double gradient with layer having a density of 1.107 g/mL at the bottom and HISTOPAQUE-1077 (2 mL each) at the top in 15 mL sterile polystyrene tubes. (The 1.107 layer was prepared by mixing appropriate volumes of HISTOPAQUE 1077 and HISTOPAQUE-1119.)

Using the same sample as in Example 1, the tubes were centrifuged at $700 \times g$ for 30 minutes. The cells at the interfaces were recovered, washed twice with PBS (phosphate buffer solution) and resuspended in HBSS.

Examination of the samples showed that in the two layer gradient gel system of Example 1, the mononuclear cells collected on the top surface, the nucleated fetal red blood cells, other nucleated fetal cells and maternal granulocytes collected at the interface between the two gel layers, and the mature red blood cells collected at the bottom of the tube. In this Example, the mononuclear cells collected on the top surface; the nucleated fetal red blood cells collected at the interface between the two gel layers; and nucleated fetal cells, maternal granulocytes and mature red blood cells collected at the bottom of the tube.

This example shows that the nucleated fetal red blood cells can be separated from a cell mixture containing mononuclear cells, granulocytes and mature red blood cells by using a discontinuous gradient gel with appropriate densities.

EXAMPLE 3

Nucleated Fetal Cell and Maternal Granulocyte Separation

A suspension of human female adult blood mixed with human fetal liver cells was prepared by mixing 7 mL of heparinized adult female blood containing $5 \times 10^9$ to $1 \times 10^{10}$ total cells with $1 \times 10^6$ fetal liver cells. The sample was diluted 1:3 with PBS.

Seven mL of this suspension was carefully layered onto a discontinuous, triple gradient with HISTOPAQUE-1119 at the bottom as the first layer, a gradient material having a density of 1.107 g/mL in the middle as the second layer (prepared by mixing HISTOPAQUE solutions) and HISTOPAQUE-1077 (1 mL each) at the top as the third layer in 15 mL sterile polystyrene tubes.

The tubes were centrifuged at $700 \times g$ for 30 minutes. The cells at all gradient interfaces were recovered, washed twice with PBS and resuspended in HBSS with 2% FCS.

Examination of the samples showed that in the three layer gradient gel system, mononuclear cells collected on the top surface, the nucleated fetal red blood cells collected at the interface between the second and third gel layers. Some nucleated cells of fetal origin and all maternal granulocytes collected at the interface between the first and second layers and the mature red blood cells collected at the bottom of the tube.

This example shows that the nucleated fetal red blood cells and a mixture of nucleated fetal cells and maternal granulocytes can be separated from blood also containing mononuclear cells and mature red blood cells by using a discontinuous gradient gel with appropriate densities.

We claim:

1. A method for separating nucleated fetal red blood cells and nucleated fetal cells and maternal granulocytes from maternal blood comprising
   a) applying maternal blood to a discontinuous gradient gel having at least first, second and third layers, the first and second layers forming a first interface therebetween, and the second and third layers forming a second interface therebetween, the first layer having a density in the range of from 1.115 to 1.125 g/mL, the second layer having a density in the range of from 1.105 to 1.110 g/mL, and the third layer having a density in the range of from 1.075 to 1.085 g/mL;
   b) exposing the gel to a separating force field for a time sufficient to cause movement of nucleated fetal cells and maternal granulocytes to the first interface and nucleated fetal red blood cells to the second interface; and
   c) removing cells from at least one of the interfaces.

2. A method of Claim 1 wherein the first layer has a density of 1.119 g/mL.

3. A method of Claim 1 wherein the second layer has a density of 1.107 g/mL.

4. A method of Claim 1 wherein the third layer has a density of 1.077 g/mL.

* * * * *